United States Patent [19]

Heinz et al.

[11] Patent Number: 5,672,200
[45] Date of Patent: Sep. 30, 1997

[54] PIGMENT PREPARATION AND ITS USE

[75] Inventors: Dieter Heinz, Heppenheim; Heinz Mohr, Speyer; Joachim Weitzel, Darmstadt, all of Germany

[73] Assignee: Merck Patent Gesellschaft Mit Beschrankter Haftung, Darmstadt, Germany

[21] Appl. No.: 579,635

[22] Filed: Dec. 26, 1995

[30] Foreign Application Priority Data

Dec. 27, 1994 [DE] Germany ............... 44 46 456.8

[51] Int. Cl.$^6$ ............ C09D 17/00; C09D 11/02; C09D 5/36

[52] U.S. Cl. ............ 106/403; 106/20 R; 106/20 C; 106/415; 106/417

[58] Field of Search ............ 106/20 R, 30 R, 106/23 C, 20 C, 415, 417, 403

[56] References Cited

U.S. PATENT DOCUMENTS

| | | | |
|---|---|---|---|
| 4,681,632 | 7/1987 | Bes et al. | 106/19 |
| 4,725,317 | 2/1988 | Wheeler | 106/403 |
| 5,407,746 | 4/1995 | Prengel et al. | 106/467 |
| 5,445,671 | 8/1995 | Herget et al. | 106/417 |

FOREIGN PATENT DOCUMENTS 2113451  10/1971  Germany ............ 106/20 C

OTHER PUBLICATIONS

Abstract of JP 62-143984. Jun. 27, 1987.

Abstract of CA 2,023,118. Jul. 17, 1991.

Abstract of DE 2,903,212. Jul. 31, 1980.

*Primary Examiner*—Melissa Bonner
*Attorney, Agent, or Firm*—Millen, White, Zelano, & Branigan, P.C.

[57] ABSTRACT

A pigment composition containing one or more luster pigments, a phosphate derivative and spherical particles having a particle size of 0.05–150 μm useful, especially, in printing inks.

19 Claims, No Drawings

PIGMENT PREPARATION AND ITS USE

The present invention relates to a pigment composition comprising one or more luster pigments, a phosphate derivative and spherical particles having a particle size of 0.05–150 μm, and to its use especially in printing inks.

BACKGROUND OF THE INVENTION

Printing inks in general consist of a binder, pigments or dyes and additives. In printed products for packaging, labels and high-quality journals, a more and more frequent requirement is to give the articles depicted a special gloss.

Printing inks containing luster pigments all have the disadvantage of having problems with print-run stability. They quickly tend to build up or sediment on the inking unit, printing plate and rubber blanket, thereby in general making a trouble-free print run of more than 10,000 sheets impossible. A basic problem is the strong tendency of luster pigments, especially pearl luster pigments, owing to their platelet-shaped structure and to their specific physicochemical surface properties, to form agglomerates in the printing ink, the pigments being stacked on top of one another with an adhesion so strong that they can be separated only with difficulty. In addition, the gloss imparted to such prints is generally not satisfactory, a fact which is to be attributed to the insufficient quantity of pigments transferred to the printed product. The ink becomes depleted in pigment as it passes through the inking unit, plate and rubber blanket. This pigment accumulates at exposed areas on the plate and blanket and leads to piling and caking.

In general, the only suitable luster pigments for printing inks are those having a very small average particle size, since the particle size is critical for pigment transfer during printing. Such pigments exist only for pearly white and pastel color effects, but not for the gold, silver, bronze and copper shades which are of great interest. The production of such color shades by the offset method using luster pigments has not hitherto been possible to achieve satisfactorily.

The use of platelet-shaped bismuth oxychloride pigments to achieve a pearl luster effect likewise does not lead to satisfactory results, since the pigment particles are highly sensitive to mechanical shear forces and are ground to destruction in the ink nip.

The use of pearl luster pigments in printing inks for offset printing is known from DE 29 03 212, which discloses the pigmentation of a commercial oil-based printing varnish with a preferably very finely divided pearl luster pigment. The offset printing varnish preparation described therein is distinguished in that the proportion of pearl luster pigments is very high, with the upper limit of the pigment concentration in the suspension being dictated essentially only by the required flow-ability of the mixture. In this preparation, the proportion of pearl luster pigments is in the range extending to 65% by weight. Varnishes having such a high proportion of pigment are highly viscous and may need to be made more flowable with a diluent, so as to be able to be processed in conventional offset printing presses. Tests have shown that, in contrast to the teaching of DE 29 03 212, with such high levels of pigmentation the transfer of pigment from the inking unit to the substrate is hampered. Print-run defects such as piling and caking occur; in other words, the achievable pearl luster effect cannot be optimized by a high level of pigmentation alone. Furthermore, the ink systems according to DE 29 03 212 do not in general exhibit an adequate dot definition, so that the ink systems described therein are limited essentially to the printing of solid areas.

SUMMARY OF THE INVENTION

An object of the invention was, therefore, to find a pigment composition in particular for printing inks, which contains luster pigments, especially pearl luster pigments, whose specific surface preparation achieves both a relatively high level of pigmentation of the printing ink and satisfactory print-run properties.

Upon further study of the specification and appended claims, further objects and advantages of this invention will become apparent-to those skilled in the art.

It has surprisingly been found that the quality of the gloss effect and the quantity of pigment particles transferred become optimal in a printing ink if a pigment composition is used which comprises one or more luster pigments, a phosphate derivative and spherical particles. These spherical particles preferably have a particle size of about 0.05–150 μm, more preferably 0.05–50 μm and, in particular, 1–30 μm.

The use of spherical particles in offset printing inks is already known from JP 62-143 984. The spherical particles described therein, of resin or wax with a diameter of 0.1–30 μm, are incorporated into the printing ink, which contains no luster pigments, by stirring in quantities of 0.1–20% by weight, in order to improve the structural properties and to prevent the picking of the paper by the rubber blanket.

In the pigment preparation according to the invention, the spherical particles prevent the plate-shaped luster pigments from piling up on one another to any notable extent in which they could exert strong adhesion. As is shown by electron micrographs, the spherical particles settle on the surface of the platelet-shaped luster pigment. Although not intending to be bound by this theory, it is believed that the spherical particles act like a kind of ball bearing, allowing the pigment platelets to move with ease with respect to one another in the printing ink, thus, very largely suppressing piling and caking of the pigments during the printing operation.

When the pigment preparation according to the invention is used in printing inks, the spherical particles may even break up existing pigment agglomerates, by action of the spherical particles being pressed into the accumulations of pigment in the course of the printing operation and causing these composite agglomerate structures to disintegrate. In the process, some of the larger spherical particles may be destroyed. Preferably, in the final print, the only particles remaining are those having a relatively small particle diameter, whereas the fragmented pieces exert a loosening effect within the composite pigment structure.

The invention therefore relates to a pigment composition comprising one or more luster pigments, a phosphate derivative and spherical particles having a particle size of preferably 0.05–150 μm.

Suitable spherical particles are, in particular, hollow spheres of glass, wax, polymers such as vinyl resins, nylon, silicone, epoxy resins, olefin resins or polystyrenes, and inorganic materials, for example $TiO_2$, $SiO_2$ or $ZrO_2$. It is preferred to use hollow spheres, although solid spheres may also be used. The spheres preferably have a particle size of from 0.05 to 150 μm. In the pigment preparation according to the invention, it is particularly preferred to employ hollow spheres of glass, wax or polymer.

Spherical particles based on $SiO_2$ in a particle range of 3–10 μm are known, for example, as materials for high-pressure liquid chromatography and are marketed, for example, as LiChrospher by Merck, Darmstadt. Such materials are preferably employed in monodisperse form, i.e.

with as uniform as possible a particle size. Mono-disperse spherical particles of this kind are known which are based on $SiO_2$, $TiO_2$ and $ZrO_2$. Monodisperse $SiO_2$, for example, can be prepared in accordance with DE 36 16 133. Hollow glass spheres are marketed, for example, under the trade name Q-CEL by PQ Corporation, USA, or Scotchlite by 3M, Frankfurt, FRG.

The improved deagglomeration of the luster pigments in a printing ink is evident even with small quantities of spherical particles in the pigment composition. For instance, even when using luster pigments having a content of 0.5% by weight of spherical particles, based on the dry pigment, significantly improved print-run properties are found in printing inks which contain the pigment composition according to the invention. In general, luster pigments having a content of preferably 1–10% by weight, in particular 1–5% by weight, of spherical particles are preferred for use in the pigment composition.

A further important component of the pigment composition according to the invention is the luster pigment. In this context, the pigment preparation may also contain a mixture of different luster pigments in order, for example to achieve specific color effects. The proportion of luster pigments in the pigment composition may be up to 99.4% by weight.

The luster pigment used preferably comprises commercial metallic pigments, such as platelet-shaped iron oxide, aluminum flakes, e.g., Standart® from Eckart, special-effect pigments, e.g., Paliochrom® from BASF, and pearl luster pigments—mica flake pigments coated with metal oxides—which are obtainable, for example, from Merck, Darmstadt under the trade name Iriodin®. The latter, for example, are known from the German patents and patent applications 14 67 468, 19 59 998, 20 09 566, 22 14 545, 22 15 191, 22 44 298, 23 13 331, 25 22 572, 31 37 808, 31 37 809, 31 51 343, 31 51 354, 31 51 355, 32 11 602 and 32 35 017. For the printing ink it is preferred to use pearl luster pigments. Those employed in particular are mica pigments coated with $TiO_2$ and/or $Fe_2O_3$, $SiO_2$ flakes, glass flakes, ceramic flakes or synthetic platelets without a support.

As a further important component, the pigment composition of the invention contains a phosphate derivative, preferably a phosphate compound, in a quantity of preferably 0.1–5% by weight, more preferably 1–3% by weight. Examples of suitable phosphate derivatives are the higher and lower metapolyphosphates and pyrophosphates. Particular preference is given to the alkali metal metapolyphosphates, especially sodium metapolyphosphate.

The pigment preparation is simple to prepare and easy to handle. The luster pigment is first mixed intensively with the spherical particles by shaking or in a dry-mixer. The phosphate derivative is then added, either stirred in as a fine particulate powder or added in the form of a suspension consisting of a salt and a liquid component. Particularly suitable liquid components are mineral oils or other non-drying oils, for example linseed oil, and also drying oils, for example soya oil, and water or organic solvents. The liquid component should in this case make up not more than 10% by weight, based on the pigment preparation. The pigment preparation can also be produced by introducing all the components simultaneously and mixing them intensively with one another. The finished pigment preparation can then be mixed into formulations such as, for example, printing inks, coatings, paints, plastics and cosmetic preparations with conventional auxiliaries thereof.

In addition to the luster pigments, phosphate derivative and spherical particles, the pigment preparation according to the invention may also contain particles of carbon black, fluorescent pigments and/or organic color pigments. In this case the composition preferably comprises 50–100% by weight of luster pigments and 0–50% by weight of carbon black particles, fluorescent pigments and/or color pigments. The total pigment content in the pigment preparation should not, however, exceed 99.4% by weight.

It is often advisable to also stir a dispersant into the pigment preparation. Dispersants which may be used are all those known to the person skilled in the art, as they are described, for example, in Karsten, Lackrohstofftabellen, 9th edition 1992. Particularly suitable dispersants are those based on polyacrylates or polymethacrylates. The quantity of the dispersant employed should not be more than 10% by weight, preferably 0.1–5% by weight.

The pigment composition according to the invention is suitable in particular for the pigmentation of printing inks. Pigmented printing inks of this kind can be employed for all known printing techniques, in particular for offset printing, letterpress printing, letterset intaglio printing, photographic printing, screen printing and also for overprinting, and additionally for coatings. They are preferably used for offset printing, in which utility they can be employed both for web-offset printing and for sheet-fed offset printing by the dry and the wet process. They are particularly suitable, however, for wet-process sheet-fed offset printing.

The pigment composition may be dispersed in the printing ink or the binder in this case by means of a stirrer mechanism with propeller or paddle stirrer, employing different dispersion temperatures, if desired. In this process, the binder envelops the pigment particles. The milled pastes which emerge from the mechanisms are subsequently made up to the finished product by addition of additives. For the preparation of a pigmented offset printing ink it is possible to use all commercial binders. Such binders consist of known synthetic or natural resins, with or without drying oils, mineral oils and additives, as described, for example, in Karsten, Lackrohstofftabellen, 9th edition 1992. The resins used preferably have a relatively low melt or solvent viscosity. However, highly polymerized and high-viscosity components may also be present. It has been found particularly appropriate to use combinations of hard resins and alkyd resins, since these provide better wetting of the luster pigments and give prints of greater gloss and rubfastness. The binders used are in particular those composed of 50–90% by weight of hard resin and 5–50% by weight of alkyd resin. The hard resins used are preferably hydrocarbon resins. The hydrocarbon resins employed my have an acid number close to 0 mg of KOH/g of solids, or else they can be modified and have acid numbers of up to 30 mg of KOH/g of solids. The binder can, in addition, contain 1–50% by weight of a mineral oil. The ink components are matched to one another so as to achieve an ink/water balance which is stable and suitable for the low ink viscosity.

The printing ink is dried by oxidative polymerization of the resins and by means of oils, for example linseed oil, wood oil or castor oil, which pass into the paper in the course of printing. The drying operation can be accelerated further by additions of drying catalysts (siccatives), which are usually fatty acid salts of cobalt, lead, manganese, etc. The proportion of drying oils in the offset printing inks according to the invention is in the range from 0–50% by weight, preferably 0–30% by weight. Further additives may be introduced into the printing ink in order to modify the ink properties for specific applications. These additives may be wax compounds, drying agents, dispersants, solvents, thickeners, lubricants, pigment fillers and/or antioxidants.

Further details regarding the fundamental characteristics of offset printing inks can be found in A. Rosenberg, Der Polygraph (11), 1153 (1987) or B. Grande, Coating (4), 38 (1987).

Frequently, very low-viscosity pigment-containing printing inks do not provide adequate dot definition. It is precisely this definition, however, which is necessary in fine screens in order to avoid clogging in the print. It is therefore advisable to provide the printing ink with structure. For instance, the addition of a structure former is able to bring about sufficient improvement in the dot definition. Preferably, the printing ink according to the invention contains in this case 0.1–3% by weight of a structure former. In addition to the improved dot definition, a printing ink modified in this way displays markedly better pigment transfer and enhanced print-run properties.

Via the choice of the resins in the binders and the proportion of luster pigments in the printing ink, it is possible to adjust individually the parameters which are critical for the printing process, such as dispersibility, tackiness and viscosity. For a given ink composition, viscosity and tackiness are mutually dependent, but may also be modified individually by a specific ink composition. In this context, it should be noted that printing inks having too high a degree of tackiness may give rise to sections of the paper tearing (picking). Inks of inadequate tackiness are not transferred in an appropriate manner in the course of the printing operation. If the penetration of the ink is too great, it becomes visible on the opposite side of the paper or causes blotchiness or lack of clarity in the reproduced image. Poorly controlled penetration may give rise to smearing and deposits. By contrast, excessively viscous inks will not flow appropriately from the filler sources to the rollers. Commercially available printing inks are formulated to viscosities in the range 12–30 Pa.s. Printing inks comprising the pigment preparation according to the invention can be formulated to viscosities <12 Pa.s, preferably <10 Pa.s, and in particular <8 Pa.s. This can be done without the printing ink exhibiting any problems in relation to spraying off from the inking rollers, even at printing speeds of 10,000 sheets per hour.

Printing inks comprising the pigment preparation of the invention are of particular importance especially with regard to graphic products of the advertising sector and for high-quality printed products, since the gloss of the finished prints means that they meet the highest of aesthetic requirements.

In order to improve the printing speeds and print-run properties it is advisable, in the case of offset printing in particular, to use impression blankets having a smooth surface, in which context the modified surface should preferably consist of polyvinyl chloride, polyurethane, polyester or Teflon and have a surface hardness of about 88°–95° Shore. The use of such an impression blanket in combination with the pigmented printing ink according to the invention ensures faultless ink transfer.

The present invention thus relates to printing inks which preferably contain up to about 40% by weight, in particular 10–30% by weight, of the pigment preparation according to the invention.

The pigment preparation according to the invention is distinguished by its high gloss and can therefore be employed for a very wide variety of purposes. In addition to its use in printing inks, it can also be employed in plastics, paints, coatings and, owing to the good skin feeling, in cosmetic preparations too.

The invention therefore relates to formulations which comprise the pigment preparation according to the invention.

The examples which follow are intended to illustrate the invention in more detail without limiting it.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. P 44 46 456.8, filed Dec. 27, 1994, are hereby incorporated by reference.

EXAMPLES

Example 1

I. Preparation of pigment

1. Dry mixing of luster pigment and spherical particles 300 g of Iriodin 123 Hellglanzsatin ($TiO_2$ mica pigment with a particle size of 5–20 μm from E. Merck, Darmstadt, FRG) are mixed with 9 g of Scotchlite S22 (hollow glass spheres having a particle size of 70 μm from 3M, Frankfurt, FRG) in a 1.5 l plastic vessel, by intense shaking.

2. Preparation of the suspension with sodium polyphosphate 100 g of Drucköl L from Kast & Ehinger, Stuttgart, FRG, and 100 g of sodium polyphosphate from E. Merck, Darmstadt, FRG are dispersed in the steel vessel of a Dispermat with a ball-milling insert (100 g of zirconium oxide balls with a diameter of 1.25–1.6 mm) for 2–3 hours at 800 revolutions with water cooling. Dispersion is complete once no coarse particles can be detected ("finger test"). The suspension is passed through a rapid sieve (E-D sieve 100 μm) and washed twice with 25 g of Drucköl L each time.

3. Production of the pigment preparation 300 g of the dry mixture from step 1 and 20 g of the sodium polyphosphate suspension from step 2 are mixed intensively with one another.

II. Preparation of a sheet-like fed offset printing ink 700 g of sheet-like fed offset binder (Gebr. Schmidt Bronzefirnis 11A10342; viscosity measured on a Laray falling-rod viscometer: about 24±2 Pa.s.) are placed in a 3 l stirring vessel with paddle stirrer. The binder is slowly stirred while 320 g of the pigment preparation from step 3 are added in portions, during which addition the mixture heats up to about 40° C. When the components are homogenously distributed, the ink is provided with an airtight seal. After storage for 24 h, the viscosity and tackiness of the ink are determined:

Eta*=20±4 Pa.s (20° C.)

Tackiness**: 120±10 (30° C.)

* Viscosity determined with a Laray falling-rod viscometer (Lhomary S.A.) following DIN 53222. Weights used: 800, 600, 400, 200 g
** Tackiness measured with a Tack-o-scope (from Test-print B.V.); roller speed 100 m/min.

Example 2

I. Preparation of pigment 720 g of Iriodin 123 are placed in a 5 l stainless steel vessel, 21.6 g of Scotchlite S22 (hollow glass spheres from 3M) are added, and intensive mixing is carried out using a Dispermat. Subsequently, a sodium polyphosphate suspension (prepared as in Example 1) consisting of 49.4 g of sodium polyphosphate and 24.7 g of Drucköl L from Kast & Ehinger is added, and all of the components are mixed intensively with one another.

II. Preparation of an offset printing ink 1400 g of offset binder (Gebr. Schmidt Bronzefirnis 11 A 1034) are introduced into a 5 l stainless steel vessel with paddle stirrer, and 680 g of the pigment preparation from I are added in portions with stirring. When the components are homogenously distributed, the ink is provided with an airtight seal. After storage for 24 h, the viscosity is measured as in Example 1 II.

Eta=4±1 Pa.s (20° C.)

Example 3—Offset printing test

Printing press: MAN Roland 202
Printing ink: Test ink from Example 1
Paper: Art paper 115 g/m$^2$
Printing plate: Ozasol P51
Blanket: Spezialdrucktuch from Streb
Damping solution: Containing 10% alcohol
Printing parameters: Plate-blanket pressure 0.2 mm
Feed pressure 0.2 mm
Inking 110%

The end product is distinguished by its high gloss. No build-up of the luster pigment-containing printing ink on the surface of the impression blanket was observed.

Example 4

I. Preparation of pigment 4.1. Dry mixing of luster pigment and spherical particles 300 g of Iriodin 123 Hellglanzsatin (TiO$_2$ mica pigment with a particle size of 5–20 μm from E. Merck, Darmstadt, FRG) are mixed with 9 g of Scotchlite S22 (hollow glass spheres having a particle size of 70 μm from 3M, Frankfurt, FRG) in a 1.5 l plastic vessel, by intense shaking.

4.2. Preparation of the suspension with sodium polyphosphate 900 g of Drucköl L from Kast & Ehinger, Stuttgart, FRG, and 600 g of sodium polyphosphate from E. Merck, Darmstadt, FRG are dispersed in the steel vessel of a Dispermat with a ball-milling insert (2 kg of zirconium oxide balls with a diameter of 1.2–1.6 mm) for 2–4 hours at 2850–3000 revolutions with water cooling. Dispersion is complete once no coarse particles can be detected ("finger test"). The suspension is passed through a rapid sieve (E-D sieve 100 μm).

II. Preparation of a sheet-like fed offset printing ink 700 g of sheet-like fed offset binder (Gebr. Schmidt Bronzefirnis 11A 1034-1; viscosity measured on a Laray falling-rod viscometer: η=12±2 Pa.s) are placed in a 3 l stirring vessel with paddle stirrer. The binder is slowly stirred while 300 g of the dry mixture from step 4.1, 20 g of the sodium polyphosphate suspension from step 4.2 and 40 g of Drucköl L from Kast & Ehinger are added in succession, during which the mixture heats up to about 50° C. When the components are homogenously distributed, the ink is provided with an airtight seal. After storage for 24 h, the viscosity and tackiness of the ink are determined:

Eta*=10±2 Pa.s (25° C.)

Tackiness**120±10 (32° C.)

* Viscosity determined with a Laray falling-rod viscometer (Lhomary S.A.) following DIN 53222. Weights used: 800, 600, 400, 200 g

** Tackiness measured with a Tack-o-scope (from Test-print B.V.): roller speed 100 m/min.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A pigment composition comprising one or more luster pigments, a metapolyphosphate compound and spherical particles having a particle size of 1–30 μm.

2. The pigment composition according to claim 1, which contains up to 99.4% by weight based on the total weight of the composition of the one or more luster pigments.

3. The pigment composition of claim 1, wherein one or more luster pigment is a pearl luster pigment.

4. The pigment composition according to claim 1, which contains the metapolyphosphate compound in a quantity of 0.1–5% by weight based on the total dry pigment composition.

5. The pigment composition according to claim 1, which contains at least 0.5% by weight of the spherical particles, based on the weight of total dry pigment composition.

6. The pigment composition according to claim 1, wherein the spherical particles are wax or polymer spheres, SiO$_2$ spheres or hollow glass spheres.

7. The pigment composition according to claim 1, further comprising not more than 10% by weight of a liquid component.

8. The pigment composition of claim 1, wherein the spherical particles are hollow spheres.

9. The pigment composition of claim 1, which contains 1 to 10% by weight, based on the total dry pigment composition, of the spherical particles.

10. The pigment composition of claim 1, which contains the metapolyphosphate compound in an amount of 1 to 3% by weight based on the total dry pigment composition.

11. The pigment composition of claim 1, wherein one or more luster pigment is a metallic pigment, special effect pigment or pearl luster pigment.

12. The pigment composition of claim 1, further comprising a carbon black pigment, fluorescent pigment or organic color pigment.

13. A printing ink, coating, paint, plastic or cosmetic composition comprising a pigment composition according to claim 1 and conventional auxiliaries.

14. A printing ink composition comprising a printing ink binder resin and a pigment composition according to claim 1.

15. The printing ink composition of claim 14, having a viscosity of less than 12 Pa.s.

16. An offset printing ink composition containing a printing ink binder resin and up to 40% by weight of the pigment composition of claim 1.

17. The pigment composition according to claim 1, wherein the spherical particles are selected from wax spheres, polymer spheres, TiO$_2$ spheres, SiO$_2$ spheres, ZrO$_2$ spheres or hollow glass spheres.

18. The pigment composition according to claim 1, wherein the spherical particles are spherical particles of a vinyl resin, nylon, silicone, epoxy resin, olefin resin or polystyrene.

19. The pigment composition according to claim 1, wherein the metapolyphosphate compound is an alkali metal metapolyphosphate.

* * * * *